(12) United States Patent
Nguyen et al.

(10) Patent No.: US 10,806,468 B2
(45) Date of Patent: Oct. 20, 2020

(54) OPTICAL CAMERA SELECTION IN MULTI-MODAL X-RAY IMAGING

(71) Applicant: KONINKLIJKE PHILIPS N.V., Eindhoven (NL)

(72) Inventors: Duc Long Nguyen, King of Prussia, PA (US); Jurgen Jean Louis Hoppenbrouwers, Boxtel (NL); Robert Johannes Frederik Homan, Batenburg (NL); Ina Klein Teeselink, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/084,876

(22) PCT Filed: Mar. 7, 2017

(86) PCT No.: PCT/EP2017/055232
§ 371 (c)(1),
(2) Date: Sep. 13, 2018

(87) PCT Pub. No.: WO2017/157715
PCT Pub. Date: Sep. 21, 2017

(65) Prior Publication Data
US 2019/0059914 A1 Feb. 28, 2019

(30) Foreign Application Priority Data
Mar. 16, 2016 (EP) ..................................... 16160568

(51) Int. Cl.
*A61B 6/00* (2006.01)
*A61B 17/17* (2006.01)
(Continued)

(52) U.S. Cl.
CPC ............ *A61B 17/1703* (2013.01); *A61B 6/12* (2013.01); *A61B 6/4417* (2013.01); *A61B 6/4441* (2013.01); *A61B 6/4482* (2013.01); *A61B 6/465* (2013.01); *A61B 6/467* (2013.01); *A61B 6/545* (2013.01); *A61B 17/00234* (2013.01); *A61B 90/361* (2016.02); *A61B 90/37* (2016.02); *A61B 5/0077* (2013.01); *A61B 90/98* (2016.02);
(Continued)

(58) Field of Classification Search
CPC .............................. A61B 5/0077; A61B 6/465
See application file for complete search history.

(56) References Cited

U.S. PATENT DOCUMENTS

| 2014/0051993 A1 | 2/2014 | McGee | |
|---|---|---|---|
| 2014/0107473 A1 | 4/2014 | Dumoulin | |
| 2014/0357989 A1* | 12/2014 | Hendriks | ............... A61B 5/066 600/424 |

FOREIGN PATENT DOCUMENTS

| WO | 2010067281 A1 | 6/2010 |
|---|---|---|
| WO | 2011063266 A2 | 5/2011 |

(Continued)

*Primary Examiner* — Dani Fox (57) ABSTRACT

A system for supporting operation of an X-ray imaging apparatus (IA) capable of assuming different imaging geometries. The system comprises an input interface (IN) for receiving a specification of a path extending at least partly into an object. A camera sampler (CS) configured to compute, for a plurality of non-ionizing radiation based cameras (OC) of the X-ray imaging apparatus (IM), a respective imaging geometry for achieving a plan view on the object along said path.

18 Claims, 3 Drawing Sheets

(51) Int. Cl.
*A61B 90/00* (2016.01)
*A61B 6/12* (2006.01)
*A61B 17/00* (2006.01)
*A61B 34/10* (2016.01)
*A61B 5/00* (2006.01)
*A61B 90/98* (2016.01)

(52) U.S. Cl.
CPC ... *A61B 2034/107* (2016.02); *A61B 2090/365* (2016.02); *A61B 2090/371* (2016.02); *A61B 2090/376* (2016.02)

(56) References Cited

FOREIGN PATENT DOCUMENTS

| WO | 2013055707 | A1 | 4/2013 |
| WO | 2014013393 | A2 | 1/2014 |

* cited by examiner

OPTICAL CAMERA SELECTION IN MULTI-MODAL X-RAY IMAGING

CROSS-REFERENCE TO PRIOR APPLICATIONS

This application is the U.S. National Phase application under 35 U.S.C. § 371 of International Application No. PCT/EP2017/055232, filed on Mar. 7, 2017, which claims the benefit of European Patent Application No. 16160568.8, filed on Mar. 16, 2016. These applications are hereby incorporated by reference herein.

FIELD OF THE INVENTION

The invention relates to a system for supporting operation of an X-ray imaging apparatus, to an imaging arrangement, to a method for supporting operation of an X-ray imaging apparatus, to a computer program element, and to a computer readable medium.

BACKGROUND OF THE INVENTION

X-ray imaging apparatuses, such as C-arm systems or other rotational systems, are used in particular in the medical field for diagnosis or during interventions to provide image based support. The later allows safe delivery at a desired location of a medical tool or instrument.

Some X-ray apparatuses include additional, non-ionizing imaging devices such as optical cameras or others. These optical cameras can provide (in addition to X-ray guidance), optical guidance during interventions. It has been observed however, that the use of such additional imaging devices in the context of X-ray imaging can sometimes necessitate inconvenient imaging geometries that interfere with the surgeon's ability to safely conduct their work.

SUMMARY OF THE INVENTION

There may therefore be a need for alternative systems and/or methods that allow more efficient operation of, in particular, a multi-modal X-ray imaging apparatus.

The object of the present invention is solved by the subject matter of the independent claims where further embodiments are incorporated in the dependent claims. It should be noted that the following described aspect of the invention equally applies to the imaging arrangement, to the method for supporting operation of an X-ray imaging apparatus, to the computer program element, and to the computer readable medium.

According to a first aspect of the invention there is provided a system for supporting operation of an X-ray imaging apparatus capable of assuming different imaging geometries, comprising:

an input interface for receiving a specification of a path extending (at least partly) into an object;

a camera sampler configured to compute, for at least one of a plurality of non-ionizing radiation based cameras of the X-ray imaging apparatus, a respective imaging geometry in which a camera achieves a plan view on the object. Specifically, in said plan view, an optical axis of the respective non-ionizing radiation based camera is aligned with said path.

In one embodiment, the system comprises:

a graphics display manager configured to effect displaying, on a display device, a graphics display including respective indications for the computed imaging geometries.

In one embodiment, the system comprises:

an event handler configured for receiving a selection event for at least one of said imaging geometries;

an imaging geometry control component configured to request modifying a current imaging geometry of the X-ray imaging apparatus to realize the selected imaging geometry.

For example, the optical camera axis may essentially coincide with the path extending into the object. This type of view is referred to as "bull's-eye-view" Yet more specifically then, and in one embodiment, the system allows the user to select which camera is to be used for the bull's-eye-view. The user is presented with a pre-view of the possible C-arm and hence X-ray detector positions (one for each optical camera) so the user can optimize their working position.

According to one embodiment the system, the graphics display comprises at least one mark-up for marking-up the indication for the at least one imaging geometry for which the selection event has been received.

According to one embodiment the graphics display manager is configured to maintain in the graphics display said mark-up until the selected imaging geometry has been assumed by the imaging apparatus.

According to one embodiment, the selection event is any of a touch screen event or an event that originates from a pointer tool signal.

In multi-modal X-ray imagers that include an additional imaging modality to help in optical or non-ionizing guidance procedures, a change in imaging geometry serves a "dual function". First, of course, the imaging geometry change is needed to acquire the relevant X-ray imagery. Second, the imaging geometry may be changed to position the additional camera means for guidance purposes. It has been observed by Applicant that in these type of imaging system, a conflict may be emerge in that a given imaging geometry, although suitable for a guidance task, may nevertheless not be optimal for user's workflow. Specifically, the imaging geometry may obstruct user's vison or there may not remain enough space between the object and the detector or other part of the imager hardware that interferes with user's tasks. The proposed system addresses this need in providing to the user a selection means to conveniently balance or reconcile user needs for space or an unobstructed view on the patient, equipment or co-workers, with a need for precise guidance especially during interventions where tools have to be precisely positioned to safeguard patient's health.

According to another aspect there is provided an imaging arrangement, comprising:

a system of as per any one of the above defined embodiments; and the X-ray imaging apparatus having the plurality of non-ionizing radiation based cameras.

According to one embodiment, the cameras are mounted at different locations of an X-ray detector unit of the X-ray imaging apparatus.

According to yet another aspect there is provided a method for supporting operation of an imaging apparatus, comprising:

receiving a specification of a path extending partly into an object;

computing, for at least one of a plurality of non-ionizing radiation based cameras of an X-ray imaging apparatus, respective imaging geometries for achieving a plan view of a camera on the object along said path. Again, in the plan view, an optical axis of the camera is aligned with said path.

According to one embodiment, the method comprises:
displaying, on a display device, a graphics display including respective indications for the computed imaging geometries.

According to one embodiment, the method comprises:
receiving a selection event for at least one of said imaging geometries;
modifying a current imaging geometry of the X-ray imaging apparatus to realize the selected imaging geometry.

"Imaging geometry" for present purposes corresponds to a certain angulation, rotation and/or translation of a gantry of the imager, such as a C-arm. The imaging geometry defines the relative spatial configuration of the X-ray detector and/or the X-ray source relative to a reference coordinate system at a reference point, such as the iso-center. Correspondingly, in embodiment with movable gantries, a change in imaging geometry is a C-arm motion (angulation and/or rotation and/or translation). At the same time, in multi-modal X-ray imagers as considered herein, the imaging geometry also defines a spatial configuration of the additional camera(s) relative to the reference point.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
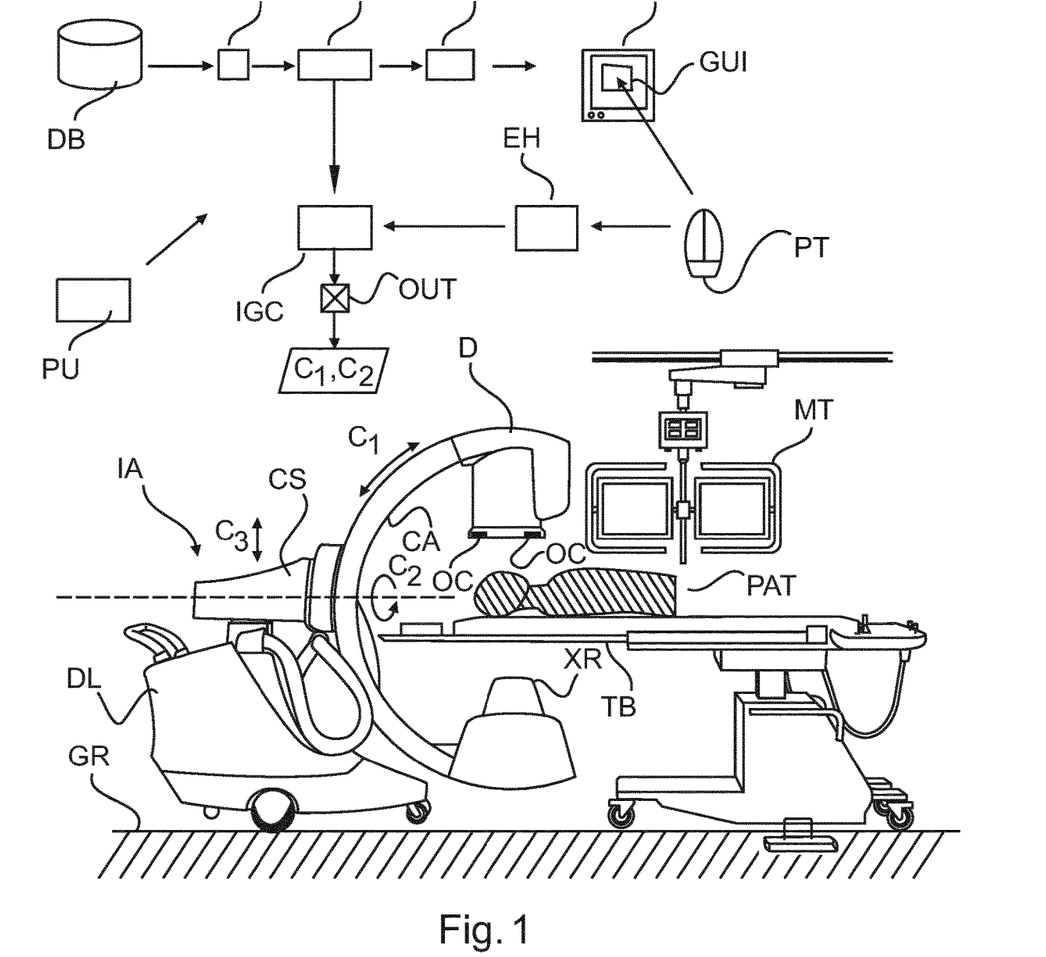
FIG. 1 shows an imaging arrangement.

FIG. 1 shows a schematic diagram of an imaging arrangement IMA. The imaging arrangement IMA comprises a rotational X-ray apparatus ("imager") IA and a system SIA for supporting operation of imager IA.

Turning first to the imager IA, this includes one or more imaging components IC. The imaging components include an X-ray source XR and an X-ray sensitive detector D. In one embodiment the rotational X-ray imager is of the C-arm or U-arm type. A combined imaging component is defined in these types of imagers where the X-ray source and the detector are connected in a stiff C-arm or U-arm structure. The C-arm CA is rotatably supported in a cradle structure CS.

As the name suggests, in these type of imagers the C-arm or U-arm is a gantry having the shape of a turned over letter "C" (or "U"). The X-ray source XR and the detector D, are respectively, connected to the respective ends of the C-arm. In this manner the gantry CA embraces at least partly an imaging region and has the X-ray source and the detector arranged in opposed relationship across said imaging region.

The imaging arrangement IA further includes in one embodiment an object support, such as a patient table TB. The object support supports an object to be imaged during the imaging procedure. In one embodiment, but not necessarily all embodiments, a medical context is envisaged where the "object" is a patient PAT or at least a part of the patient's anatomy. Human or animal patients are envisaged herein. The object however may also be inanimate such as an item of baggage in screening applications or the object may be a sample in non-destructive application, etc. Although in the following we will refer mainly to the medical context, this is not to exclude these (and other) non-medical contexts.

The image apparatus IA in FIG. 1 shows a mobile solution with the cradle structure mounted in a moveable dolly structure DL. However this is exemplary, as fixed solutions are also envisaged where the C-arm is rotatably ceiling, floor or wall mounted or mounted on a cradle fixedly connected to the ground GR of the imaging venue (examination room, etc).

The imaging apparatus enjoys a number of different mechanical degrees of freedom to help a user achieve best imaging results ("user" we refer to the person operating the imager). For instance, and as shown in FIG. 1, the combined imaging component (that is, the C-arm with the source XR and detector D connected therein) is rotatable not only about a single axis, but two or more rotation axes although embodiments with a single rotational degree of freedom are not excluded herein.

One rotation axis is shown in FIG. 1 as a dashed line. It allows rotation essentially about the longitudinal axis of the patient when lying on the patient table TB. This first rotation is indicated by C2 in the Figure.

There is also another rotation envisaged herein referred to in the following as "angulation". This rotation is around an axis which extends perpendicular into the plane of the drawing of FIG. 1. That is, the axis for the angulation is perpendicular to the longitudinal axis of the patient. The angulation is shown as C1. In addition to having the one or more rotation axis, the cradle structure is height adjustable relative to ground GR.

Other translation options are also included and envisaged in other embodiments. In one, but not necessarily all embodiments, it is also or instead, the table TB that is height adjustable. The adjustable table height is shown as H2 in FIG. 1.

The respective translations or rotations (in particular the angulation) are brought about by suitable actuators (not shown) such as stepper motors or servo motors suitable arranged and controlled from an operator console CON. The console CON includes one or more user control interfaces such as a joystick, foot pedal or other. When the user, such as an interventional radiologist, operates the user interface of the console, a series of commands are issued. These are translated into electrical control signals with which the various actuators can be controlled and adjusted.

The control signals correspond to requests for a certain imaging geometry. By the term "imaging geometry" is meant the specific spatial configuration between the imaging components and the patient. The imaging geometry can be changed by rotating the C-arm around the one or more axis, in particular by angulation and/or by changing the image component height H1 relative ground.

Broadly, during the imaging procedure, the user requests a certain imaging geometry by operating the console and issues the control signals to the respective actuators. In response thereto it is in particular the C-arm's angulation and/or height that are adjusted to achieve the best possible view of the anatomy of interest. Once the desired imaging geometry is assumed, that is, once the C-arm has moved into place, the X-ray source is operated to emit an X-ray radiation beam which passes through the anatomy of interest. The X-ray beam interacts with matter in the anatomy. The interacting X-ray emerges at the far end (relative to the X-ray source) from the patient and then impinges on an X-ray sensitive surface of the detector D. The surface is made up from detector pixels. These respond to the impinging radiation by generating a spatially corresponding image signal. The image signals are captured by data acquisition circuitry which includes in particular an analogue to digital converter stage to produce imagery which can be viewed on one or two monitors MT.

Imagery acquirable by the imager IA includes projection images or 3D rotational 3D volume imagery reconstructable by suitable reconstruction algorithms from a series projection images acquired in a rotation round the object at different projection angles.

The X-ray imaging apparatus IA further includes a plurality of non-ionizing radiation based cameras such as optical cameras OC that capture light in the visible spectrum though suitable sensor technology such as CCDs (charged coupled device). Preferably, industry-grade digital cameras with low latency read-outs (in the order of 60 ms) are used to allow quick imaging. Other camera types based on other technologies such as infrared cameras or depth sensing cameras are also envisaged in some embodiments.

For instance, as shown in FIG. 1, the optical cameras OC are fixedly and immovably attached to the detector unit D of the imaging apparatus IA. The view in imager IA as per inset FIG. 1A is taken along an optical axis of the x-radiation detector D in a direction from the X-ray source XR towards the detector D to so afford a plan view of the proximal face of the detector unit D.

Figure 1A:
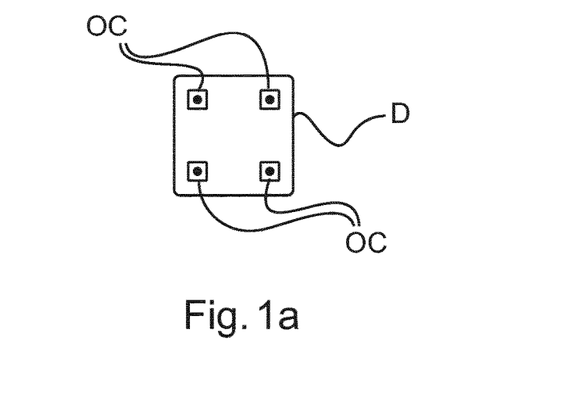

In the embodiment of FIG. 1A, there are four optical cameras which are arranged in respective corners of the detector unit around the field of view (FOV) of the detector D. More specifically, the cameras OC are arranged around an ingress window (not shown) of the detector unit D through which the X-ray radiation passes in its way to a radiation sensitive surface of the detector unit D. The cameras OCs may also be arranged along the edges (eg, at center points of the edges) of the FOV rather than at FOV corners as shown. The housing may have a round profile rather than the square or rectangular profile shown in FIG. 1A. For round housings, the cameras may be arranged at regular distances along the round periphery of the field of view.

In FIG. 1A, the optical cameras OC are integrated into the housing of the detector. In other embodiments, the cameras OC are attached from the outside to the housing by suitable fittings to depend downwardly (towards the X-ray source XR) from the housing.

The number of cameras may vary from four as shown in FIG. 1A. In other embodiments there are two, three, or more than four cameras. In general, the number of cameras is suitable to measure 3D position, In alternative embodiments the optical cameras are attached to other parts of the imager IA hardware, such as on suitable locations of the C-arm itself or are attached to other parts of the detector unit.

In the above described embodiments, the cameras OC are immovably coupled to the X-ray imager so have no mechanical degrees of freedom relative to the remainder of the imager IA hardware, in particular to the X-ray detector D. Position and orientation of the cameras can only be changed by motion of the detector D, which, in a preferred embodiment, is effected through C-arm motion.

Other, alternative, embodiments are also envisaged, where the optical axis of at least one or all of the cameras can be changed relative to the detector D. For instance, a camera may be translatable relative to the detector D. The detector housing may include tracks along which the camera can translate. In addition, or alternatively, some cameras may be arranged in a swivel mechanism so that an orientation of the camera (ie, its optical axis) can be changed relative to the detector D. If the position or orientation of the cameras can be changed relative to the detector D, this can be achieved with suitable electro-mechanical actuators operable by the user through suitable camera control user interfaces, preferably arranged in ergonomically close proximity to the user controls for the C-arm.

The cameras OC afford efficient path planning. In more detail, the optical cameras are used herein for live guidance in respect of a planned path for an intervention. An exemplary medical intervention where the cameras OC can be put to use is guidance in spinal fusion surgery. In spinal fusion surgery, one or more pedicle screws are introduced into the patient from the outside through the soft tissue and into the respective vertebra of the spinal column to render two neighboring vertebrae immovable relative to each other. This may be done for pain relief purposes for instance. Because in a preferred embodiment the cameras OC are immovably mounted relative to the detector D, there is natural (rigid) image registration, and the X-ray imagery acquired by the X-ray detector can be overlaid on the optical images acquired by the optical cameras and this can be done with high accuracy. In the so overlaid imagery corresponding image features of an organ are correctly aligned, with the optical image showing an outer anatomy (eg skin) of the underlying, internal, anatomy (eg, a vertebra) as per the X-ray image. If position or orientation of optical cameras relative to the detector D can be changed, an additional image registration processing may have to be applied.

During the procedure, the user plans the position/orientation of an instrument (like a pedicle screw) to be introduced using an acquired 3D volume (for example, of the relevant spinal vertebrae). In this "virtual" planning procedure, a graphical representation of the instrument is indicated/drawn into the 3D volume. The 3D volume is correctly registered relative to a common coordinate system of the X-ray imaging apparatus. The 3D volume is reconstructed from projection images previously obtained of the object by the imaging apparatus IA. The planned position/orientation of the instrument may also be overlaid as a graphical representation on the optical image. The user can now virtually align the instrument (its graphical representation that is) with the planned position/orientation on the optical images and achieve a high accuracy when placing the instrument. During the alignment of the instrument, the C-arm is positioned such that one of the cameras is exactly above the planned path. In this way the path is now visible in plan view as a point or circle, the diameter of which corresponds to the thickness of the path. This view is called "bull's eye view". In this way, an entry point for the instrument on the skin of the patient can be found easily.

More particularly, in bull's-eye-view (BEV), an individual optical axis of a given one of the cameras is aligned with the planned path, preferably aligned so as to essentially coincide with a direction of the planned path. Only one camera can be aligned for the same BEV at a time. As mentioned earlier, the orientation and position of any one of the cameras (as measured relative to the patient's anatomy of interest or relative to the iso-center of the imaging system) can be changed by changing the imaging geometry of the imaging system. More particularly, by changing angulation and rotation of the C-arm and/or by translating the C-arm, a corresponding re-orientation and/or shift of the optical axis of the camera relative to the object can be achieved. In this manner, each camera, for a given BEV, is unambiguously associated with exactly one imaging geometry, respectively, and these imaging geometries will be different for every camera because the cameras are mounted at different locations on to the imager IA. In the following, a respective imaging geometry that affords a bull's eye view for exactly one of the plurality of cameras, will be occasionally referred to herein as "bull's-eye-view imaging geometry" or, more palpably by using the acronym introduce above, "BEV imaging geometry".

Because the cameras OC are located at different positions on the X-ray detector or elsewhere on the imager IA hardware, the BEV imaging geometries are different as mentioned earlier, and some of these will be more suitable and will afford a better view for the user on the object or allow for more space between the detector and the object.

Now, in order to make the operation of the X-ray imaging apparatus more efficient for the user, a system is proposed herein which allows the user to select which camera, from the plurality of cameras OC, is to be used to acquire the bull's eye view.

The proposed system comprises a plurality of components which may be run as a software application on a single computing or data processing unit PU such as a workstation associated with the imager IA. Alternatively, the components may be distributed across a wireless or wired (or a hybrid of both) network of computing devices. In other embodiments, the proposed system to support efficient operations of the X-ray apparatus may be realized as dedicated hardware equipment such as a programmed FPGA (field-programmable-gate-array) or as a hardwired IC or other micro-controller integrated into the X-ray imaging apparatus.

Operation of the proposed system is as follows. At input port IN a specification of the geometry of planned path is received. The specification is in general in coordinate form relative to a coordinate system located at the iso-center of the imager AI. The specification includes in particular a location of the entry point and the length and direction of the planned path and, possibly, its thickness or diameter.

Given the path specification, a camera sampler CS computes for each of the plurality of cameras, the required imaging geometry which affords the same bull's-eye-view on the path via the respective camera. Because location and orientation of the cameras is known relative to the imager IA hardware, the required imaging geometry can be readily computed. This is true in particular if the cameras are immovably mounted to the detector D or other parts of the imager hardware as described above. The BEV imaging geometries computed by the camera sampler CS are then output as a set of co-ordinates. In one embodiment each of these coordinates specify, for the respective camera i, the required C-arm angulation/rotation/translation required to achieve the bull's eye view.

This BEV information is then represented in numerical or graphical form on which the user can then conveniently act on. For instance in one embodiment the system comprises a graphics display manager GDM. The graphics display generator GDM combines a plurality of graphical widgets to form a graphics display GUI which can be displayed on one or more monitors MT. More particularly, the graphic display manager generates a graphics display GUI which includes a plurality of indications IG1-IG4 for the respective imaging geometries at which the bull's eye view can be obtained by the respective camera.

Preferably, these indications are interactive graphical widgets so that the user can quickly select the imaging geometry which suits best to their current position relative to the patient and would afford maximal working space and/or unobstructed view on patient, equipment or by-standing co-workers.

Figure 2:
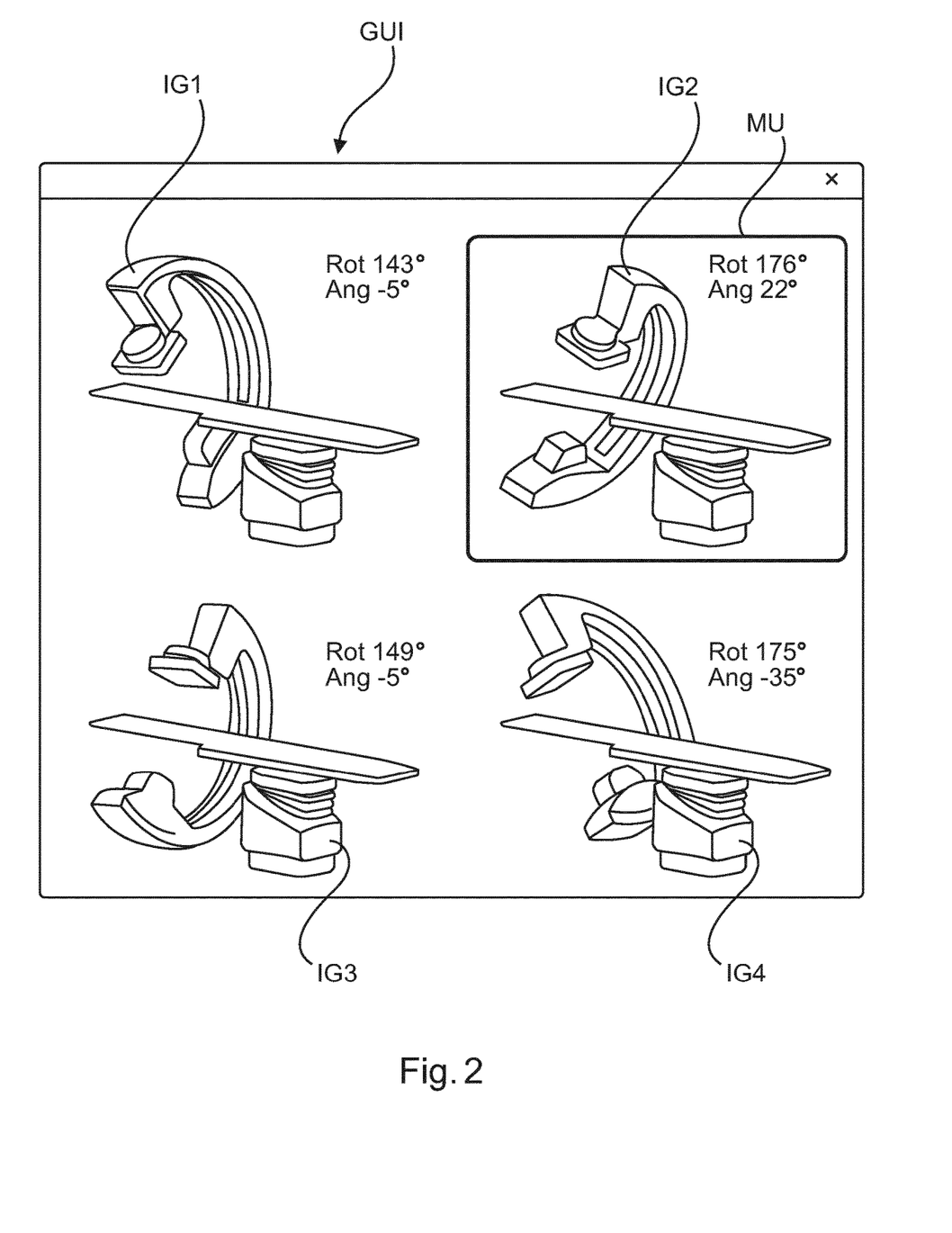
FIG. 2 shows a graphics display representing different imaging geometries of an imaging apparatus.

FIG. 2 shows an exemplary embodiment for such a graphics display GUI. The graphics display is preferably interactive and implemented on a touch screen. The graphics display GUI includes four panes, one for each of the cameras OC, and in each there is rendered a representation IG1-IG4 of the respective BEV imaging geometry associated with the respective camera.

In one embodiment, some or all panes include numerical information that specifies the BEV imaging geometry in terms of rotation and angulation angle. In addition to the numeric information or instead of this, the indication IG1-IG4 comprises a graphical icon, such as a miniature, that represents the imaging geometry so that the user can better visualize whether and how the proposed imaging geometries may or may not affect the user's vision on the patient or other surrounding equipment, etc given user's current position. In one embodiment, the graphical indications IG1-IG4 for the respective BEV imaging geometries are adjoined with symbology that represents said current user position. For instance, symbolic "foot-print" icons or others may be displayed in correct spatial relationship to the represented BEV imaging geometries in the indications IG1-IG4. The current user position can be collected by suitable sensor circuitry arranged around the imager IA. For instance, a pattern of inductive loops may be laid out on the floor. These respond with position readings depending on where the user stands. The readings are then rendered by the graphics display manager GDM for display by including the user position widget (eg, the mentioned footprint icon or other) at the correct location in the BEV widgets IG1-IG4. Optionally, the system may further include a verification (sub-) system to distinguish whether it is the user's presence that causes the position readings or whether the readings are caused by other persons, such as nurses etc. In one embodiment, the verification system includes suitably positioned RFDI readers or similar and the user wears an RFID tag encoded with a specific code. The position readings issued by the loop are only processed by the graphics display manager GDM if presence of the code is detected by the reader. Otherwise the position readings are ignored. However, other embodiments of the verification system are also envisaged, such as proximity sensor based and others.

In one embodiment the indications are not static but dynamic. For instant, the miniatures are not merely static symbology but are themselves animations that represent the movement involved from changing from the current imaging geometry to the BEV affording ones. The respective animations in the respective panes can be run in sync at the same time, or can be run in sequence. The animations may be run once, or may run repeatedly. The user can stop the animation or can request a certain one or all of the animations to be re-run.

The graphics display GUI further includes a mark-up widget MU that indicates a currently selected one of the imaging geometries displayed in the graphics display. In the example of FIG. 2, it is the imaging geometry in the upper right hand that is currently selected as shown by the highlighted border. Other widgets can be used to indicate a current selection. For instance, rather than highlighting the border regions, it is the respective pane canvas itself that may be changed into a different color or pattern that stands out against the surrounding background canvas. In either case, and more generally, visualization of the selection mark-up MU can be by highlighting through color, texture/pattern work, grey tones or other.

In one embodiment, there is a default selection of the BEV imaging geometry. In one embodiment this default selection is for the BEV imaging geometry which will entail the least motion from the given, current imaging geometry.

In other embodiments where there is no C-arm and where the detector and/or X-ray source are independently ceiling or wall mounted on respective arms, the respective graphical indications for the BEV imaging geometries will need to be adapted accordingly.

As mentioned earlier, a selection of the individual geometries can occur by touch screen event by the user touching the respective bull's eye imaging geometry widget IG1-IG4 or by using a pointer tool PT such as a stylus, computer mouse or otherwise. Alternatively, the selection may also be requested by keyboard-stroke.

Once the user or a protocol performs a selection act (eg, touch screen action), a selection event/signal is generated which is intercepted by an event handler EH. The event handler EH generates a request to change the current imaging geometry for the selected one and this command is then forwarded to an imaging geometry control component IGC. The imaging geometry control IGC component is an interface which is capable of translating the requested BEV imaging geometry co-ordinates into a corresponding lower level request (C1,C2) which is then propagated to one or more of the actuator circuitry in the imaging apparatus IA. The actuators then effect the requested BEV imaging geometry, eg, by C-arm re-orientation and or translation.

As a security measure, the generated graphics display GUI remains displayed until the requested X-ray imaging geometry is assumed and is only then no longer shown on the monitor. This enhances safety of operation, because the user receives visual real-time information on when the requested BEV imaging geometry is actually assumed. This is helpful in situations where the user must actively control the imaging geometry change. For instance, in some systems the C-arm moves only whilst an activation button is pressed. More particularly, the user enables the movement of the C-arm to the requested position by pushing a so-called "Accept" button. The presented dialog GUI with the 4 different positions IG1-IG4 will disappear automatically if the system detects that the system is moving to the selected position.

It will be appreciated that the proposed system for support of X-ray imaging operation or handling can also be used in other interventional procedures that are based on optical guidance and where tools or instruments need to be inserted in a pre-defined manner into the patient, such as electrodes, needle, catheters, etc.

It will be further appreciated that the application of the proposed imaging support system is not confined to the medical field but can also be used with benefit in other fields such as probe insertion in all kinds of investigations such as non-destructive material testing or others.

According to one embodiment, there is no graphics module manager, as the coordinates for the computed BEV imaging geometries are suppled purely in numerical format.

Figure 3:
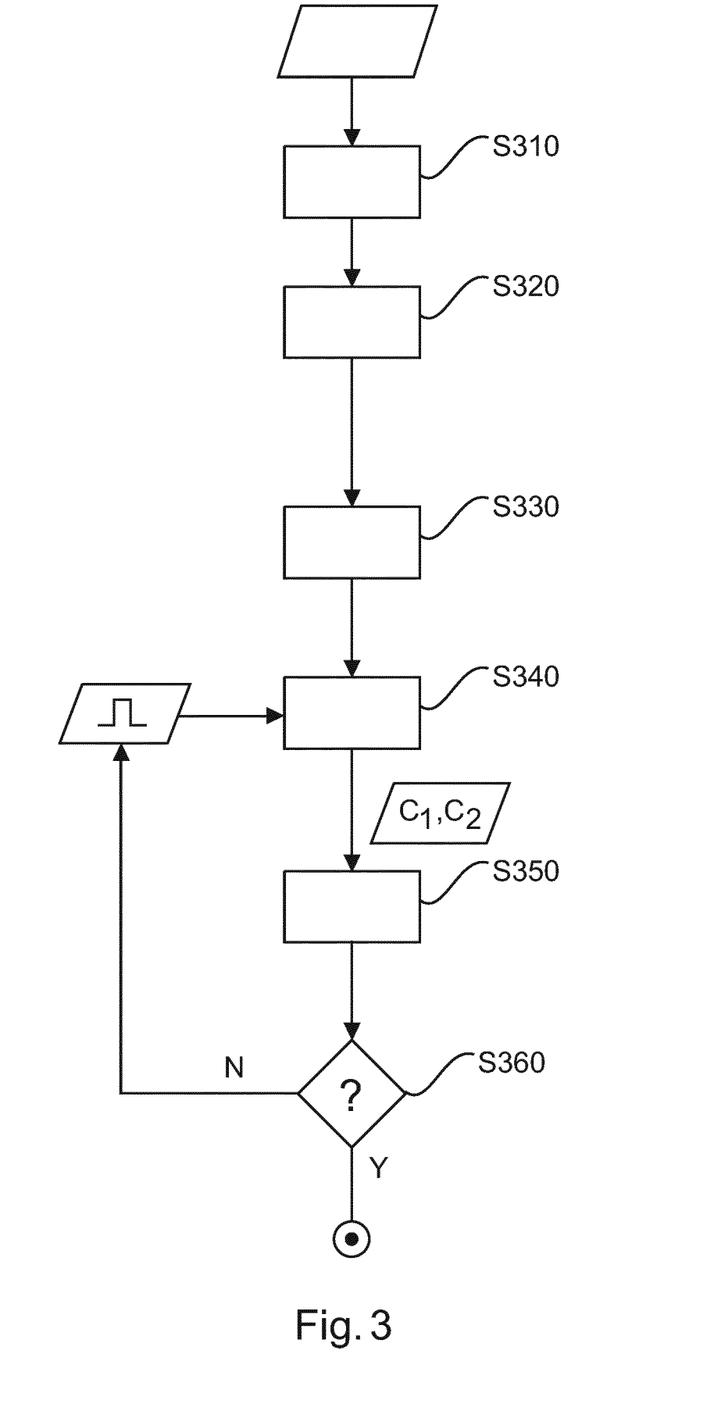
FIG. 3 shows a method for operating an imaging apparatus.

Reference is now made to FIG. 3, which shows a flow chart for supporting an operation of an X-ray imaging apparatus including additional non-ionizing imaging devices such as optical cameras or others.

At step S310 a specification of a path extending partially into an object is received. This specification specifies in particular a length, entry point and orientation and optionally a thickness of the path. It is assumed herein that the path is a straight line although the proposed method may also be used for at least slightly curved paths. In case of curved path, guidance cannot be guaranteed however throughout the whole course of the path but merely at an initial segment thereof.

At step S320, respective imaging geometries are computed for each (or a user defined pre-selection) of the plurality of cameras. Each of the imaging geometries allows aligning a respective one of the cameras so that a bull's eye view on the same path is obtained.

The respective imaging geometries can be readily computed for hardware embodiments, such as the one shown in FIG. 1A, where the cameras are immovably fixed to the imager hardware IA, such as to the detector unit. In this or similar arrangements, no registration is required because there is a known, constant, rigid registration relationship between the camera position/orientation and the remaining imager hardware. If some or all of the cameras are independently movable, an additional registration step is required to compute the BEV imaging geometries.

At step S330 a graphics display for display on a display device (such as a tablet, smart phone or a stand-alone computer monitor) is generated. The generated graphics display includes respective graphical indications that indicate the respective imaging geometries.

At step S340 a selection event, for instance generated by the user or by a protocol, is received for at least one of the imaging geometries represented by the respective indications in the graphics display generated at step S330.

At step S350 the selected bull's eye imaging geometry is then realized by changing a current imaging geometry for the requested one by operation of suitable actuators.

As a safety feature, respective graphical indicators, for instance mark-ups, can be integrated into the graphics display to visually represent the current selection. An example of this is shown in FIG. 2.

As a further safety feature, the mark-up for the selection and/or the whole of the graphics display remains displayed until the requested geometry is actually assumed. Once this has happened a corresponding confirmation signal is issued by the system which in turn instructs the graphics display manager to remove the graphics display from the screen.

Optionally, there is a looping operation step S360 that loops to intercept an additional selection event as the user may not be happy with the selected BEV imaging geometry once actually assumed. If the user issues a new selection event, flow returns to step S340. Otherwise the method flow terminates.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for supporting operation of an X-ray imaging apparatus adapted to assume different imaging geometries, the system comprising:
an input interface for receiving a specification of a path extending at least partly into an object; and
a camera sampler configured to compute, for at least one of a plurality of non-ionizing radiation based cameras of the X-ray imaging apparatus, a respective imaging geometry of the X-ray imaging apparatus in which the at least one of the plurality of non-ionizing radiation based cameras achieves a plan view on the object, an optical axis of said camera being aligned with said path in said plan view.

2. The system of claim 1, comprising:
a graphics display manager configured to effect displaying, on a display device, a graphics display including a respective indication or the computed imaging geometry.

3. The system of claim 2, comprising:
an event handler configured for receiving a selection event for at least one of said imaging geometries; and
an imaging geometry control component configured to request modifying a current imaging geometry of the X-ray imaging apparatus to realize the selected imaging geometry.

4. The system of claim 2, wherein the displayed graphics display comprises at least one mark-up for marking-up the indication for the at least one imaging geometry for which the selection event has been received.

5. The system of claim 2, wherein the graphics display manager is configured to maintain in the graphics display said mark-up until the selected imaging geometry has been assumed by the imaging apparatus.

6. The system of claim 3, wherein the selection event is any of a touch screen event or an event that originates from a pointer tool signal.

7. A method for supporting operation of an X-ray imaging apparatus adapted to assume different imaging geometries, comprising:
receiving a specification of a path extending partly into an object; and
computing, for at least one of a plurality of non-ionizing radiation based cameras of the X-ray imaging apparatus, a respective imaging geometry of the X-ray imaging apparatus in which the at least one of the plurality of non-ionizing radiation based cameras achieves a plan view on the object, an optical axis of said camera being aligned with said path in said plan view, an optical axis of said camera being aligned with said path in said plan view.

8. The method of claim 7, comprising:
displaying on a display device a graphics display including respective indications for the computed imaging geometry.

9. The method of claim 8, comprising:
receiving a selection event for at least one of said imaging geometries; and
modifying a current imaging geometry of the X-ray imaging apparatus to realize the selected imaging geometry.

10. An imaging arrangement, comprising:
an X-ray imaging apparatus comprising a plurality of non-ionizing radiation based cameras adapted to assume different imaging geometries;
an input interface adapted to receive a specification of a path extending at least partly into an object; and
a camera sampler configured to compute, for at least one of the plurality of non-ionizing radiation based cameras, a respective imaging geometry of the X-ray imaging apparatus in which the at least one of the plurality of non-ionizing radiation based cameras achieves a plan view on the object, wherein an optical axis of the camera is aligned with said path in said plan view.

11. The imaging arrangement of claim 10, wherein the cameras are mounted at different locations of an X-ray detector unit of the X-ray imaging apparatus.

12. The imaging arrangement of claim 10, further comprising:

a graphics display manager configured to effect displaying, on a display device, a graphics display comprising a respective indication or the computed imaging geometry.

13. The imaging arrangement of claim 12, further comprising:
    an event handler configured to receive a selection event for at least one of said imaging geometries; and
    an imaging geometry control component configured to request modifying a current imaging geometry of the X-ray imaging apparatus to realize the selected imaging geometry.

14. The imaging arrangement of claim 12, wherein the displayed graphics display comprises at least one mark-up for marking-up the indication for the at least one imaging geometry for which the selection event has been received.

15. The imaging arrangement of claim 12, wherein the graphics display manager is configured to maintain in the graphics display said mark-up until the selected imaging geometry has been assumed by the imaging apparatus.

16. A controller for supporting operation of an X-ray imaging apparatus adapted to assume different imaging geometries, the controller comprising:
    a processor;
    a tangible non-transitory computer readable medium that stores instructions, which when executed by the processor, causes the controller to:
    receive a specification of a path extending partly into an object; and
    compute, for at least one of a plurality of non-ionizing radiation based cameras, a respective imaging geometry of the X-ray imaging apparatus in which the at least one of the plurality of non-ionizing radiation based cameras achieves a plan view on the object, wherein an optical axis of the at least one of the plurality of radiation based camera is aligned with said path in said plan view.

17. The controller of claim 16, wherein the instruction when executed by the processor further cause the controller to display on a display device a graphics display including respective indications for the computed imaging geometry.

18. The controller of claim 17, wherein the instruction when executed by the processor further cause the controller to receive a selection event for at least one of the imaging geometries; and modify a current imaging geometry of the X-ray imaging apparatus to realize the selected imaging geometry.

* * * * *